(12) United States Patent
Berkulin et al.

(10) Patent No.: US 6,395,308 B1
(45) Date of Patent: May 28, 2002

(54) **PURIFIED EXTRACT FROM *HARPAGOPHYTUM PROCUMBENS* AND/OR *HARPAGOPHYTUM ZEYHERI* DENCE**

(75) Inventors: Willi Berkulin, Ransbach-Baumbach; Frauke Gaedcke, Koblenz, both of (DE)

(73) Assignee: Finzekberg GmbH & Co. KG, Andermach (DE)

( * ) Notice: Subject to any disclaimer, the term of this patent is extended or adjusted under 35 U.S.C. 154(b) by 0 days.

(21) Appl. No.: 09/147,271

(22) PCT Filed: May 15, 1997

(86) PCT No.: PCT/EP97/02491

§ 371 (c)(1),
(2), (4) Date: Mar. 24, 1999

(87) PCT Pub. No.: WO97/44051

PCT Pub. Date: Nov. 27, 1997

(30) Foreign Application Priority Data

May 18, 1996 (DE) .......................................... 196 20 052

(51) Int. Cl.[7] .......................... A01N 43/04; A61K 31/70
(52) U.S. Cl. .......................................... 424/725; 514/25
(58) Field of Search .............................. 424/195.1, 93.7, 424/725; 514/783, 25; 435/410, 420, 431; 210/634, 511, 542

(56) References Cited

U.S. PATENT DOCUMENTS

| | | | | |
|---|---|---|---|---|
| 3,856,946 A | * | 12/1974 | Debat .......................... 424/195 |
| 3,878,299 A | * | 4/1975 | Vilain et al. ................. 424/195 |
| 4,440,760 A | * | 4/1984 | Newnham .................... 424/184 |
| 4,795,742 A | * | 1/1989 | Liu .............................. 514/26 |
| 5,589,182 A | * | 12/1996 | Tashiro et al. .............. 424/423 |
| 5,733,551 A | * | 3/1998 | Jacob et al. ............. 424/195.1 |
| 5,888,514 A | * | 3/1999 | Weisman ................. 424/195.1 |
| 5,910,307 A | * | 6/1999 | Kwak ...................... 424/195.1 |

FOREIGN PATENT DOCUMENTS

| | | |
|---|---|---|
| EP | 0 524 873 A | 1/1993 |
| FR | 2 614 791 A | 11/1988 |
| KR | 9305686 | 11/1989 |

OTHER PUBLICATIONS

French Pat 1791 English Abst., 1988.*
Jaspersen, Harpagophyti radix—is it a Wonder–Drug. (Question).), Schweiz.Apoth.Ztg., 127, No. 11, see the abstract only, 1989.*
Caparasse, M., *J. Pharm. Belg.*, "Description, Identification Et Usages Thérapeutiques De La <<Griffe Du Diable>>: Harpagophytum Procumbens DC (*)", Mar. 2, 1980 vol. 35, No. 2, 143–149.

* cited by examiner

*Primary Examiner*—David M. Naff
*Assistant Examiner*—Deborah K. Ware
(74) *Attorney, Agent, or Firm*—Jacobson Holman, PLLC

(57) ABSTRACT

A purified extract from *Harpagophytum procumbens* and/or *Harpagophytum zeyheri* DENCE is obtainable by dissolving an aqueous and/or aqueous/alcoholic extract in water saturated with n-butanol, extracting with n-butanol saturated with water, and removing the n-butanol in vacuo. It may be used for the preparation of medicaments for the treatment of Asthma bronchiale, Colitis ulcerosa, Morbus Crohn, diseases of the rheumatic type, and indications in which an increase of the lipoxygenase level occurs either by medicaments, other substances or diseases.

3 Claims, 2 Drawing Sheets

PURIFIED EXTRACT FROM *HARPAGOPHYTUM PROCUMBENS* AND/OR *HARPAGOPHYTUM ZEYHERI* DENCE

BACKGROUND OF THE INVENTION

Teas and extracts from *Harpagophytum procumbens* have long been recommended in the folk medicine for various indications, for example, indigestions of different kinds, rheumatic diseases, obstetrics, wound healing, arterial calcification, allergic diseases, etc.

There have been extensive reports on the plant, its components and their chemical structures; in contrast, pharmacological/toxicological works are found much less often. A literature survey can be found in Erfahrungsheilkunde 2, 1995, pages 74 to 79. Studies with various extracts of the secondary root with water, methanol and n-butanol can be found in A. Erdös et al. in "Planta medica", Journal of Medicinal Plant Research, 1978, vol. 34, pages 97 to 108. This work supports earlier findings according to which such extracts exhibit a medium-potent, significantly analgetic activity which is lower, however, than that of acetylsalicylic acid. Further, this work is also led to the conclusion that the glycoside harpagoside is probably not the only substance to account for the analgetic and antiphlogistic effects achieved. Evidence of this is furnished by the activity of the highly purified extract H 25 $C_3$ which contains 85% of harpagoside, but fails to exhibit a significantly better effect than the other extracts in all of the experimental models.

From reviews dealing with the suitability of extracts from Radix Harpagophyti in treatments of rheumatic diseases (Wenzel, P., Wegener, T., DAZ 135, 1131–1144), it can be seen that Harpagophytum extracts have medium-potent analgetic and strong anti-phlogistic activities. For both indication areas, as a rule, a mechanism of action is claimed which is experimentally determined by the inhibition of cyclooxygenase activity (Simmet et al., Thrombosis Res. 67, 123–134, 1992).

SUMMARY OF THE INVENTION

It has been the first object of the invention to provide a purified and as well as possible standardized extract from *Harpagophytum procumbens* which possibly has a higher efficiency than highly purified harpagoside. It has been a further object of the invention to employ other suitable starting materials as well.

These objects have now been surprisingly achieved by extracts obtainable by dissolving aqueous and/or aqueous/alcoholic ($C_1$–$C_3$) *Extract spissum* and/or dry extracts in water saturated with n-butanol, extracting with n-butanol saturated with water, and removing the n-butanol in vacuo. The n-butanol is removed as completely as possible. It has further been established that, in addition to *Harpagophytum procumbens*, *Harpagophytum zeyheri* DENCE can be used with virtually equal success. Thus, it is by all means possible to employ these two starting drugs alone or in admixture.

Figure 1:
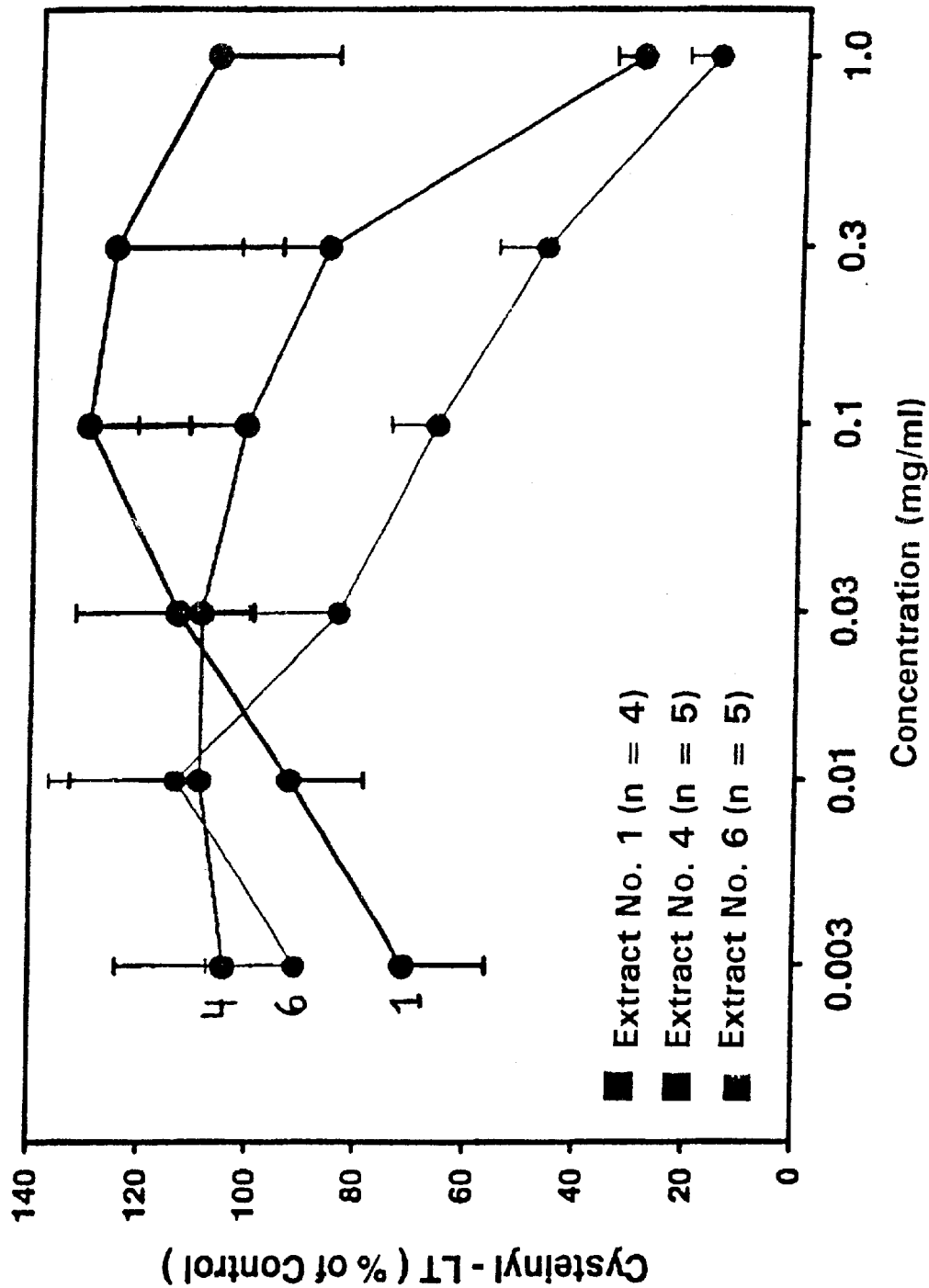
FIGS. 1 and 2 are graphs, which summarize comparative test results reported in the instant specification.

It has remained unclear to date why such extracts are more effective than the extracts which have been known and used before. From the literature, it could not be anticipated that a process would be successful which results in a high enrichment of harpagoside since this glycoside by itself is evidently not or only weakly effective. One possible explanation which has not been proven to date is that the actually active principle is not the harpagoside, but a substance or group of substances which at least partially is entrained with it when being highly purified. Another possible explanation is that there are one or more accompanying substances which act synergistically wherein this synergism itself can have various causes. These could be either a second or more substances which are also effective, or one or more substances which increase the bioavailability or stability of the harpagoside in the gastrointestinal tract. Finally, substances which antagonistically affect the activity could be depleted or removed from the multicomponent mixture by the process according to the invention.

One of these explanations is supported by the fact that chromatographic examinations of the aqueous extract, the aqueous/alcoholic extract, the n-butanol extract and the extracts according to the invention are clearly distinct. According to the invention, the content of harpagoside is of the same order as in the extract from pure n-butanol. However, the effectiveness of the pure n-butanol extract is clearly lower than that of the extracts according to the invention. Water or water/alcohol ($C_1$–$C_3$) mixtures might be capable of extracting the actually active principle or the synergistically acting principle from the plant material in a high yield. Then, after it has been extracted, it is also readily soluble in n-butanol and is thus enriched together with the harpagoside.

Although it has not been established to date whether harpagoside alone is active at all, its content can be used for "standardizing" the preparation according to the invention. Further work which has not yet been completed is aiming at finding out whereupon the better antiphlogistic and analgetic activities of the extracts according to the invention are based. It may then even be possible to elucidate whether the activity is based on the second substance or group of substances alone or whether there is a synergism with harpagoside.

In practice, however, it is already a significant progress to provide a purified and highly effective, standardizable extract which can be prepared from both *Harpagophytum procumbens* and *Harpagophytum zeyheri* DENCE.

These extracts can be first processed into oral application forms, for example, tablets, capsules, juices, syrups or solutions.

Thus, the present invention not only pertains to the purified extracts, but also to the process for their preparation and to their use in the preparation of medicaments for the treatment of Asthma bronchiale, Colitis ulcerosa, Morbus Crohn, diseases of the rheumatic type and indications in which an increase of the lipoxygenase level occurs either by medicaments, other substances or diseases.

The process according to the invention will be illustrated in more detail by the following examples:

EXAMPLE 1

200 kg of dried secondary storage roots of *Harpagophytum procumbens* and/or *Harpagophytum zeyheri* DENCE is comminuted in a mill to a grain size of smaller than 12 mm, preferably from 8 to 10 mm. After the addition of 2100 kg of water, the mixture is thoroughly percolated at 70 to 85° C. for 16 h. The extract thus obtained is brought to a dry substance content of 65 to 75% at 55° C. under reduced pressure of 150 mbar. The harpagoside content is from about 1.0 to 1.5%.

The aqueous pilular extract of about 180 kg thus obtained (primary extract) is admixed with tenfold its dry content of water saturated with n-butanol. The extract is completely dissolved with stirring and subjected to liquid/liquid extraction with equal volume fractions of n-butanol saturated with water at about 30° C. This is followed by phase separation. The lower, aqueous phase is subjected two more times to liquid/liquid extraction with each half the volume of n-butanol.

The butanol phases obtained from the three individual extraction steps are combined and rewashed with water saturated with butanol. The combined butanol phase is subsequently evaporated at about 50 to 60° C. under reduced pressure of 150 to 200 mbar until a concentrate having a solids content of at least 50% is obtained.

The pilular extract of about 16 kg thus obtained (secondary extract) is dried native on a spray-drying aggregate at 60 to 80° C. The n-butanol is practically completely removed. The resulting dry extract is ground. The dry extract according to the invention has a harpagoside content of about 15 to 30% from HPLC and has a drug-to-extract ratio (DER) of from about 25 to 35:1.

EXAMPLE 2

The aqueous pilular extract of about 180 kg obtained according to example 1 (primary extract) is dried at about 80° C. in a spray-drying process. By treating in a vertical mixer for 30 min and subsequent grinding to finest grain size of <1 mm, a homogeneous dry extract (primary extract) is prepared. This dried aqueous extract of *Harpagophytum procumbens* and/or *Harpagophytum zeyheri* DENCE is dissolved in about tenfold of water saturated with n-butanol (starting solution). This starting solution is filtered and partitioned with an equal volume of n-butanol saturated with water. Phase separation occurs. The upper, butanol phase is rewashed with water saturated with butanol (ratio of 1:1 v/v). The lower, aqueous phase is extracted two more times, i.e. a total of three times, with butanol saturated with water. The combined butanol phases are evaporated to dryness in vacuo (200 mbar, 60° C.). The aqueous phases are also combined and concentrated. A comparative examination of the starting solution, the water phase and the butanol phase gave the following results:

| parameter | starting solution | water phase | butanol phase |
|---|---|---|---|
| harpagoside content from HPLC [%] | 0.21 | n.d. | 2.25 |
| dry substance content (DS) [%] | 8.9 | 2.9 | 12.0 |
| calculated harpagoside content in DS m/m [%] | 2.36 | — | 18.75 |
| amount of native extract [g] | 17.80 | 15.72 | 2.02 |
| yield of extracted material [%] | — | 88.4 | 11.4 |
| amount of harpagoside [g] | 0.42 | — | 0.38 |
| yield of harpagoside [%] | — | — | 90.5 |
| $DER_{native}$ | 1.8:1 | — | 15.8:1 |

From this table, it can be seen that liquid/liquid extraction with butanol saturated with water results in selective enrichment of harpagoside, yielding similar concentrations as in a pure butanol extraction.

However, in the process according to the invention, the major amounts of dry substance and the secondary materials contained therein, such as sugar, remain in the aqueous phase whereas harpagoside, other iridoid compounds and other active ingredients are transferred to the n-butanol phase.

EXAMPLE 3

200 kg of dried secondary storage roots of *Harpagophytum procumbens* DE CANDOLLE and/or *Harpagophytum zeyheri* DENCE is comminuted in a mill to a grain size of from 8 to 10 mm. After the addition of about 3600 kg of 90% (v/v) ethanol, the mixture is thoroughly percolated at 20 to 30° C. for 16 h. The extract thus obtained is brought to a dry substance content of <95% at 55° C. under reduced pressure of 150 mbar. This yields 20 to 30 kg of dry extract having a DER of from 6 to 12:1. The harpagoside content is from about 1 to 1.5. The Extr. Harpagophytum e rad. spir. sicc. of about 180 kg thus employed is further processed as described in example 1

The harpagoside content is 11.6 m/m [%], the amount of native extract is 0.9 g, and the yield of extracted material is 8.6%. The amount of harpagoside is 0.112 g. The yield is 93.4%. The drug-to-extract ratio $DER_{native}$ is 3:1 in the starting solution and 32:1 in the butanol phase.

Thus, this extract also contains highly enriched harpagoside. The HPLC chromatogram of the extract thus obtained is very similar to that of the extract according to examples 1 and 2.

Comparative pharmacological studies by Professors Simmet and Loew with an aqueous-only extract, an n-butanol-only extract and an extract according to the invention revealed a clearly higher effectiveness of the extracts according to the invention as compared to the pure n-butanol extract which has a comparable concentration of harpagoside.

The following extracts were examined:

| No. of extract | extractant | $DER_{native}$ | harpagoside content [%] |
|---|---|---|---|
| 1 | water | 2:1 | 2.4 |
| 4 | 100% water-saturated n-butanol | 10:1 | 11.6 |
| 6 | n-butanol extract of 1 (example 2) | 15.8:1 | 18.8 |

Figure 2:
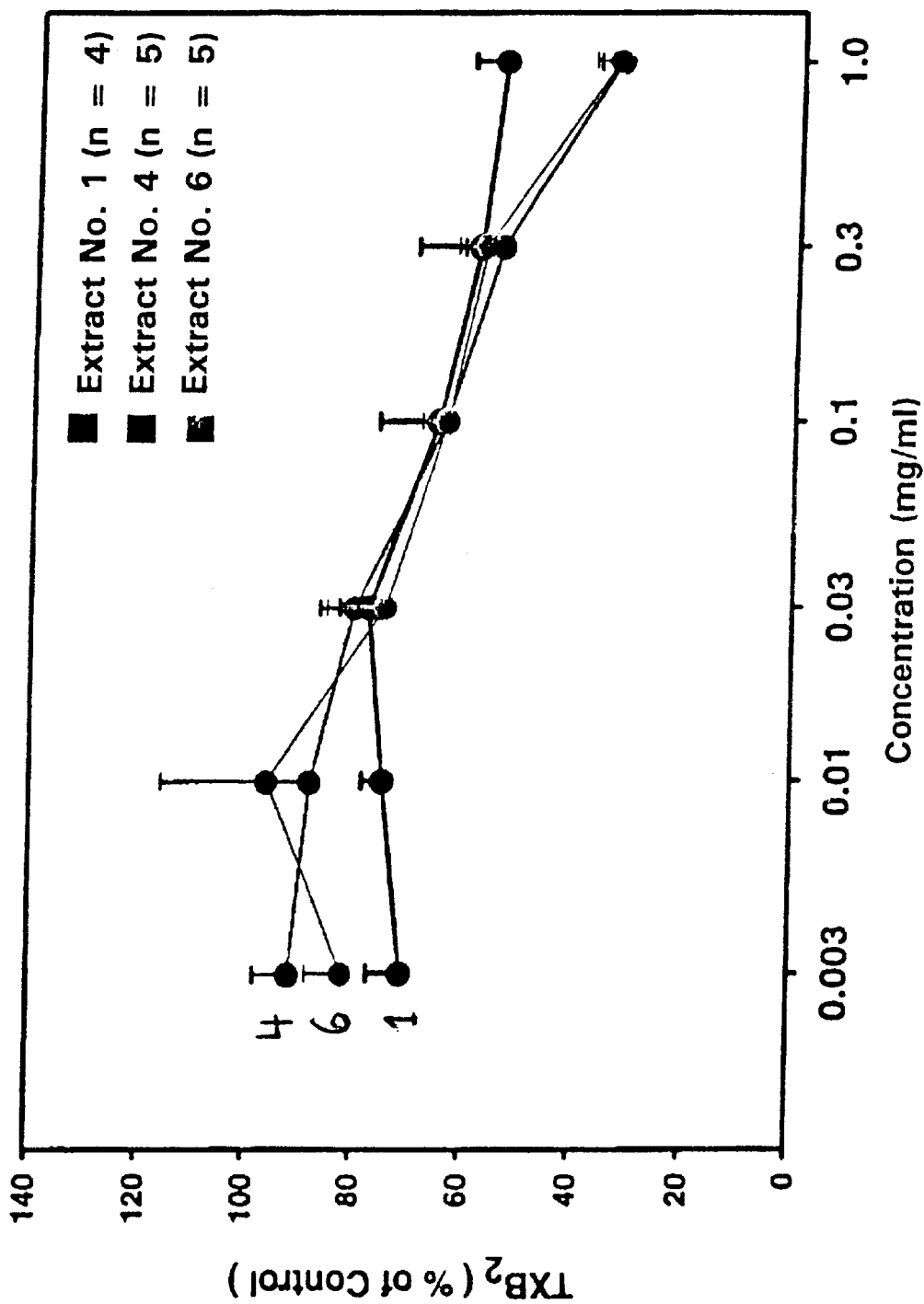

The influence of the extracts on cysteinyl-LT biosynthesis and thromboxane $B_2$ biosynthesis has been examined. 2 ml each of whole blood from healthy male subjects (20 to 25 years old) were anti-coagulated with heparin, 10 E/ml (final concentration), and preincubated with the respective test extract at 37° C. in polystyrene tubes for 15 min. After this period, Ionophor A23187, 10 μM (final concentration), was added and the incubation continued at 37° C. for another 60 min. After centrifugation, the plasma was removed, one aliquot was retained, and protein precipitation was performed with precooled acetone (−20° C., 30 min). The samples were then concentrated on a Rotavapor under reduced pressure and resuspended in 10 mM tris buffer, pH 7.4. This material was used for radioimmunological analysis of the cysteinyl-leucotrienes (LT). The anti-cysteinyl-LT antibodies mainly recognize $LTC_4$, but exhibit each 70% of cross-reaction with $LTD_4$ and $LTE_4$. The standard curves had been established with $LTC_4$. Thromboxane (TX) $B_2$ was directly determined by radioimmunology in aliquots of the plasma samples. The results are summarized in FIGS. 1 and 2.

It results that the effects on thromboxane $B_2$ biosynthesis are comparable whereas the effects on cysteinyl-LT biosynthesis are clearly different, and that the extract No. 6 according to the invention is clearly more effective and more selective.

It results therefrom that the extract according to the invention can be used for the indications Asthma bronchiale, Colitis ulcerosa, Morbus Crohn, diseases of the rheumatic type and indications in which an increase of the lipoxygenase level occurs either by medicaments, other substances or diseases.

Further pharmacological studies with an extract with 100% methanol (extract No. 5), in contrast, exhibited no significant effect on cysteinyl-LT biosynthesis whereas the extract according to example 3 (extract No. 8) showed a similarly high activity as extract No. 6 according to example 2.

Studies with artificial gastric juice and artificial intestinal juice showed that harpagoside is stable for at least two hours both in pure form and in diluted form. Pharmacokinetically studies showed that the highest blood levels are observed within a period of 1 to 4 hours after intake with administered quantities of between 200 and 800 mg of the extract according to example 2.

What is claimed is:

1. A purified plant extract, said plant being *Harpagophytum procumbens* and/or *Harpagophytum zeyheri* DENCE, obtainable by the process comprising the steps of:
   a) preparing an aqueous extract or an aqueous/$C_1$–$C_3$ alcoholic extract of a dried root of said plant;
   b) drying said extract to obtain a dried extract;
   c) dissolving said dried extract in water saturated with n-butanol to obtain a solution;
   d) subjecting the solution to liquid/liquid extraction with n-butanol saturated with water to obtain an n-butanol phase and an aqueous phase as a two-phase mixture; and
   e) removing the n-butanol from the two-phase mixture, in vacuo, to obtain a dry extract having a harpagoside content of about 15–30%, as determined by HPLC, as said purified plant extract.

2. A method for treatment of Asthma bronchiale, Colitis ulcerosa, Morbus Crohn or rheumatic diseases, said method comprising administering to a patient the purified plant extract according to claim 1.

3. A process for the preparation of a purified plant extract, said plant being *Harpagophytum procumbens* and/or *Harpagophytum zeyheri* DENCE, comprising the steps of:
   a) preparing an aqueous extract or an aqueous/$C_1$–$C_3$ alcoholic extract of a dried root of said plant;
   b) drying said extract to obtain a dried extract;
   c) dissolving said dried extract in water saturated with n-butanol to obtain a solution;
   d) subjecting the solution to liquid/liquid extraction with n-butanol saturated with water to obtain an n-butanol phase and an aqueous phase as a two-phase mixture; and
   e) removing the n-butanol from the two-phase mixture, in vacuo, to obtain a dry extract having a harpagoside content of about 15–30% as determined by HPLC, as said purified plant extract.

* * * * *

UNITED STATES PATENT AND TRADEMARK OFFICE
CERTIFICATE OF CORRECTION

PATENT NO. : 6,395,308 B1
DATED : May 28, 2002
INVENTOR(S) : Berkulin et al.

It is certified that error appears in the above-identified patent and that said Letters Patent is hereby corrected as shown below:

<u>Title page,</u>
Item [75], Inventor, change the first inventor's city of residence from "Ransbach-Baumbach" to -- Alsbach --.

Item [73], Assignee, change the assignee's name from "Finzekberg GmbH & Co." to -- Finzelberg GmbH & Co. --.
Change the assignee's city from "Andermach" to -- Andernach --.

Signed and Sealed this

Twenty-seventh Day of August, 2002

*Attest:*

JAMES E. ROGAN
*Attesting Officer*   *Director of the United States Patent and Trademark Office*